United States Patent
Goodwin

(10) Patent No.: US 7,141,801 B2
(45) Date of Patent: Nov. 28, 2006

(54) SYSTEM AND METHOD OF ILLUMINATING LIVING CELLS FOR IMAGING

(75) Inventor: Paul C. Goodwin, Shoreline, WA (US)

(73) Assignee: Applied Precision, LLC, Issaquah, WA (US)

( * ) Notice: Subject to any disclaimer, the term of this patent is extended or adjusted under 35 U.S.C. 154(b) by 75 days.

(21) Appl. No.: 10/742,456

(22) Filed: Dec. 19, 2003

(65) Prior Publication Data

US 2004/0186516 A1   Sep. 23, 2004

Related U.S. Application Data

(60) Provisional application No. 60/436,776, filed on Dec. 26, 2002.

(51) Int. Cl.
*G01J 1/58* (2006.01)
(52) U.S. Cl. ............... 250/458.1; 250/459.1; 356/317; 356/318; 356/417
(58) Field of Classification Search ........... 250/227.21, 250/458.1, 459.1; 356/317, 318, 417
See application file for complete search history.

(56) References Cited

U.S. PATENT DOCUMENTS

| | | | | |
|---|---|---|---|---|
| 5,923,466 A | * | 7/1999 | Krause et al. | 359/389 |
| 6,252,236 B1 | * | 6/2001 | Trulson et al. | 250/458.1 |
| 6,558,958 B1 | * | 5/2003 | Pilevar et al. | 436/518 |
| 6,614,031 B1 | * | 9/2003 | Engelhardt et al. | 250/459.1 |
| 6,953,927 B1 | * | 10/2005 | Quake et al. | 250/234 |

* cited by examiner

*Primary Examiner*—Stephone B. Allen
*Assistant Examiner*—Davienne Monbleau
(74) *Attorney, Agent, or Firm*—Pillsbury Winthrop Shaw Pittman LLP

(57) ABSTRACT

A system and method of providing illumination for a cell imaging system delivering modulated light for illumination of a sample. Modulation of illumination intensity may be effectuated by pulsing the output of a light source, for example, or by selectively interrupting light provided by the source. Such modulated illumination may have particular utility in applications where reducing the number of electrons in a super-excited state may minimize the rate of photobleaching and photodamage in the molecules being studied.

25 Claims, 7 Drawing Sheets

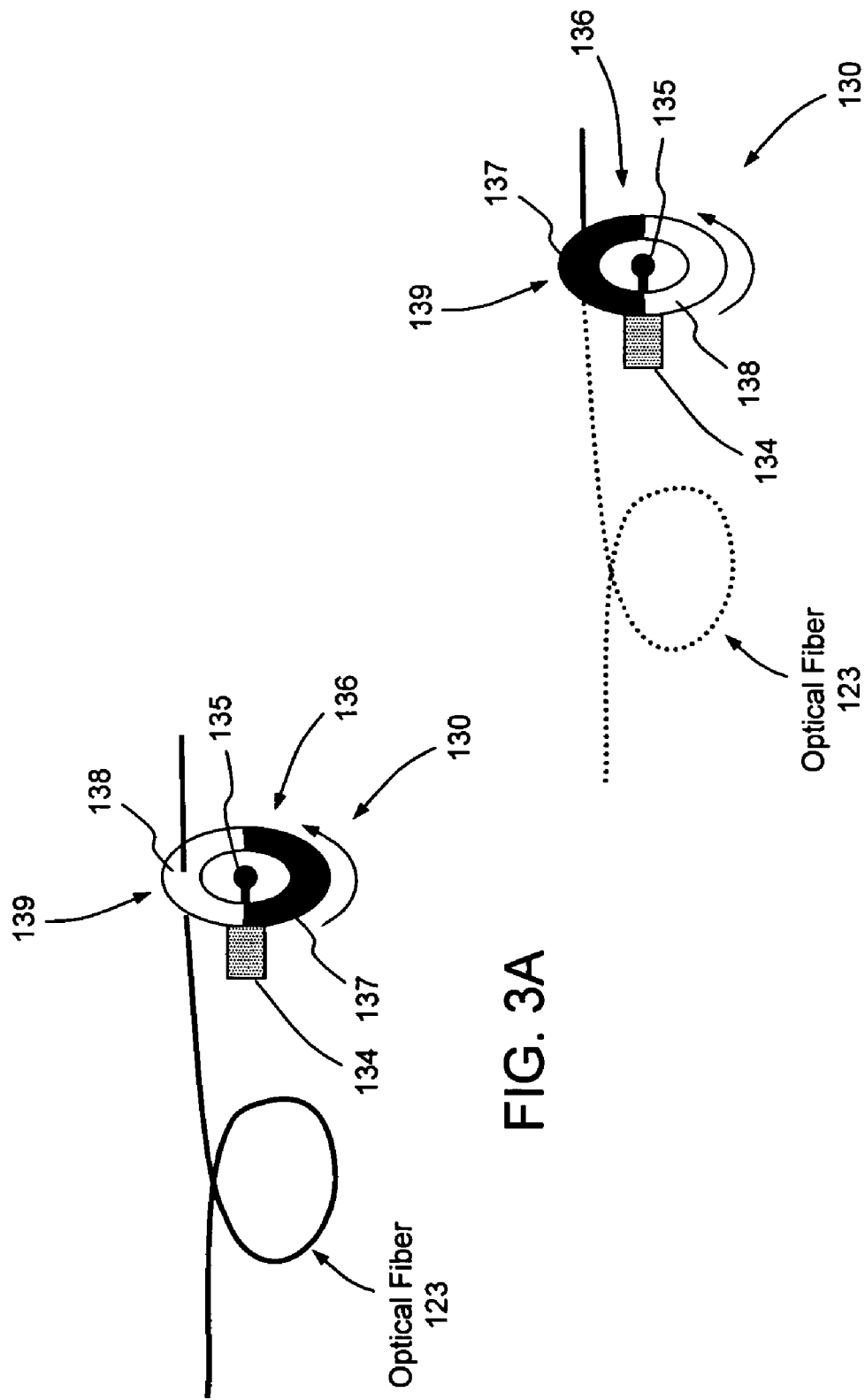

US 7,141,801 B2

SYSTEM AND METHOD OF ILLUMINATING LIVING CELLS FOR IMAGING

CROSS-REFERENCE TO RELATED APPLICATIONS

The present application claims the benefit of U.S. provisional application Ser. No. 60/436,776, filed Dec. 26, 2002, entitled "SYSTEM AND METHOD OF ILLUMINATING LIVING CELLS FOR IMAGING."

FIELD OF THE INVENTION

Aspects of the present invention relate generally to illuminating living cells for imaging, and more particularly to a system and method of providing modulated illumination intensities in fluorescence microscopy applications.

DESCRIPTION OF THE RELATED ART

Fluorescence microscopy is well described in the art and is commonly used for the examination of biological materials. Fluorescence microscopy has also been used to examine living cells since at least the 1960's. More recently, researchers have demonstrated that Green Fluorescent Protein (GFP) can be expressed in eukaryotic cells, that GFP can form chimeric proteins in these cells, and that the GFP assembled in eukaryotic cells retains its fluorescence. Numerous peer-reviewed publications have set forth the benefits attendant with using fluorescence microscopy techniques in these and similar applications.

Conventional fluorescence microscopy techniques for examining living cells suffer from at least two significant limitations: photobleaching; and photodamage. In photobleaching, the fluorescence of the target molecule being studied is reduced over time by oxidation of the fluorochrome. In photodamage, the presence of electrons in their excited states (a requisite for fluorescence) leads to formation of free-radicals that damage the very cells that are being studied.

Fluorescence was first observed by George Stokes in 1852. Fundamentally, fluorescence emissions occur when molecules absorb energy and re-emit that energy (minus some energy loss) in the form of light. One common illustration used to explain this process is referred to as a Jablonski Diagram, generally represented in FIG. 6. As the Jablonski Diagram indicates, the absorption of energy, for example, in the form of a photon, may cause excitation of an electron; such excitation tends to elevate the electron to a higher shell. This condition—wherein an electron occupies a higher than normal electron shell—is generally referred to in the art as the "excited state" with respect to the molecule, in general, or to the excited electron, in particular. Excitation in this context is extremely fast, occurring on the order of femtoseconds ($10^{-15}$ seconds). Additionally, an excited electron may be converted to a slightly greater or lesser energy state through a process, generally referred to as "internal conversion," that occurs on the order of picoseconds ($10^{-12}$ seconds). Eventually, on the order of hundreds of microseconds ($10^{-8}$ seconds), the excited electron may fall to its normal state (the ground state). In the process of returning to the ground state, the electron will emit a photon of light with less energy than the one that was initially absorbed to cause the excitation event. This process of photon emission is called fluorescence.

The electron remains in the excited state for a relatively long time. While the electron remains in the excited state, interactions that can degrade fluorescence may occur. One of the more common interactions occurs between an electron in the excited state and an oxygen molecule. Such interactions generally result in formation of a species called a "super-oxide." Super-oxides can attack the fluorescent molecule itself, causing its fluorescence to diminish or to fail altogether; this degradation of fluorescence is the photobleaching effect. Additionally or alternatively, such super-oxides may interact with other molecules, such as the proteins within the cell; this interaction with cellular components leads to photodamage. These interactions occur on the time scale of nanoseconds ($10^{-9}$ seconds).

Further, if a molecule is re-excited while already in the excited state (a condition referred to as "super-excited"), electrons remain in the excited state for a prolonged period of time, increasing the probability that they will interact to form super-oxides and lead to photobleaching and photodamage. It is desirable, therefore, to minimize re-excitation of excited electrons as a mechanism for minimizing the coincidence of molecules in the super-excited state and thereby controlling super-oxide formation which may contribute to deleterious photobleaching and photodamage in fluorescence microscopy and other applications.

SUMMARY

Embodiments of the present invention overcome the above-mentioned and various other shortcomings of conventional technology, providing a system and method of delivering pulsed or modulated light for illumination of a sample. Though not limited to any specific system environment or structural context, such modulated illumination may have particular utility in live-cell imaging applications where reducing the coincidence of multiply excited electrons (i.e., reducing the number of molecules in a super-excited state) may minimize the rate of photobleaching and photodamage in the molecules being studied. In that regard, aspects of the present invention may facilitate reduction of both the photobleaching and the photodamage effects induced during the process of fluorescence microscopy.

In accordance with some embodiments, for example, a method of delivering pulsed or modulated light for illumination of a sample may generally comprise: providing illumination from a source; selectively modulating an intensity of the illumination at a frequency operative to reduce re-excitation of excited sample molecules; and delivering the illumination to an imaging system in accordance with the selectively modulating. In one exemplary implementation, the re-excitation reducing frequency is greater than the excitation half-time of fluorophores in the sample molecules up to one tenth of the shutter exposure rate.

Selectively modulating an intensity of the illumination may comprise pulsing the intensity of the illumination at the re-excitation reducing frequency. In that regard, the pulsing may comprise varying an output of illumination from the source during the providing operation, such as by utilizing a non-continuous wave laser or a light emitting diode, for example.

In some embodiments, selectively modulating may comprise interrupting the providing at the re-excitation reducing frequency. As set forth in more detail below, such the interrupting may comprise utilizing a mechanical device or an electro-mechanical device. Additionally or alternatively, the interrupting may utilize electrical interruption of the providing from the source.

In one embodiment, a system configured and operative in accordance with the present disclosure comprises: an imaging system; an excitation light delivery system comprising an illumination source; the delivery system operative to deliver illumination from the source to illuminate sample molecules at the imaging system; and a modulation mechanism for selectively modulating an intensity of the illumination at a frequency operative to reduce re-excitation of excited ones of the sample molecules.

The modulation mechanism may comprise a mechanical apparatus, such as a rotating light chopper or micro-mirror, for example, interposed between the source and the imaging system. In some implementations, the modulation mechanism is coupled to the source and comprises an electrical mechanism operative to vary an output of illumination from the source; as noted above, the source may be a non-continuous wave laser or a light emitting diode.

In accordance with one exemplary embodiment, a system for illuminating live cells may comprise: an illumination source; an imaging system operative to acquire images of sample molecules; an excitation light delivery path delivering illumination from the source to illuminate the sample molecules at the imaging system; and a modulation apparatus interposed between the source and the imaging system in the delivery path; the modulation apparatus modulating an intensity of the illumination at a frequency operative to reduce re-excitation of excited ones of the sample molecules. As set forth herein, such a modulation apparatus may be embodied in a light chopper or a digital micro-mirror.

In an alternative embodiment, a system operative in accordance with the present disclosure comprises: an illumination source; and an imaging system receiving illumination from the source and operative to acquire images of sample molecules; wherein the source modulates an intensity of the illumination at a frequency operative to reduce re-excitation of excited ones of the sample molecules. The foregoing system may employ a source embodied in or comprising a pulsed laser or a light emitting diode.

The foregoing and other aspects of various embodiments of the present invention will be apparent through examination of the following detailed description thereof in conjunction with the accompanying drawings.

BRIEF DESCRIPTION OF THE DRAWINGS

FIGS. 3A and 3B are simplified block diagrams illustrating structural components of one embodiment of a modulation apparatus.

DETAILED DESCRIPTION

Aspects of the present invention pertain generally to a system and method of illumination allowing live-cell imaging with reduced photobleaching and photodamage effects. As set forth above, the longer electrons remain in the excited state, the more likely they are to form reactive chemical species such as super-oxides that lead to photobleaching and photodamage; in that regard, re-excitation of electrons that are already excited prolongs that excited state. As set forth in more detail below, if the excitation of the fluorochrome is pulsed or modulated at an appropriate frequency, however, each fluorochrome may be provided an opportunity to relax (i.e., return to the ground state and fluoresce) prior to re-excitation. The embodiments set forth below generally relate to a system and method of pulsing or otherwise modulating the intensity of illumination at a frequency operative to reduce such deleterious re-excitation of excited molecules or electrons.

Figure 1:
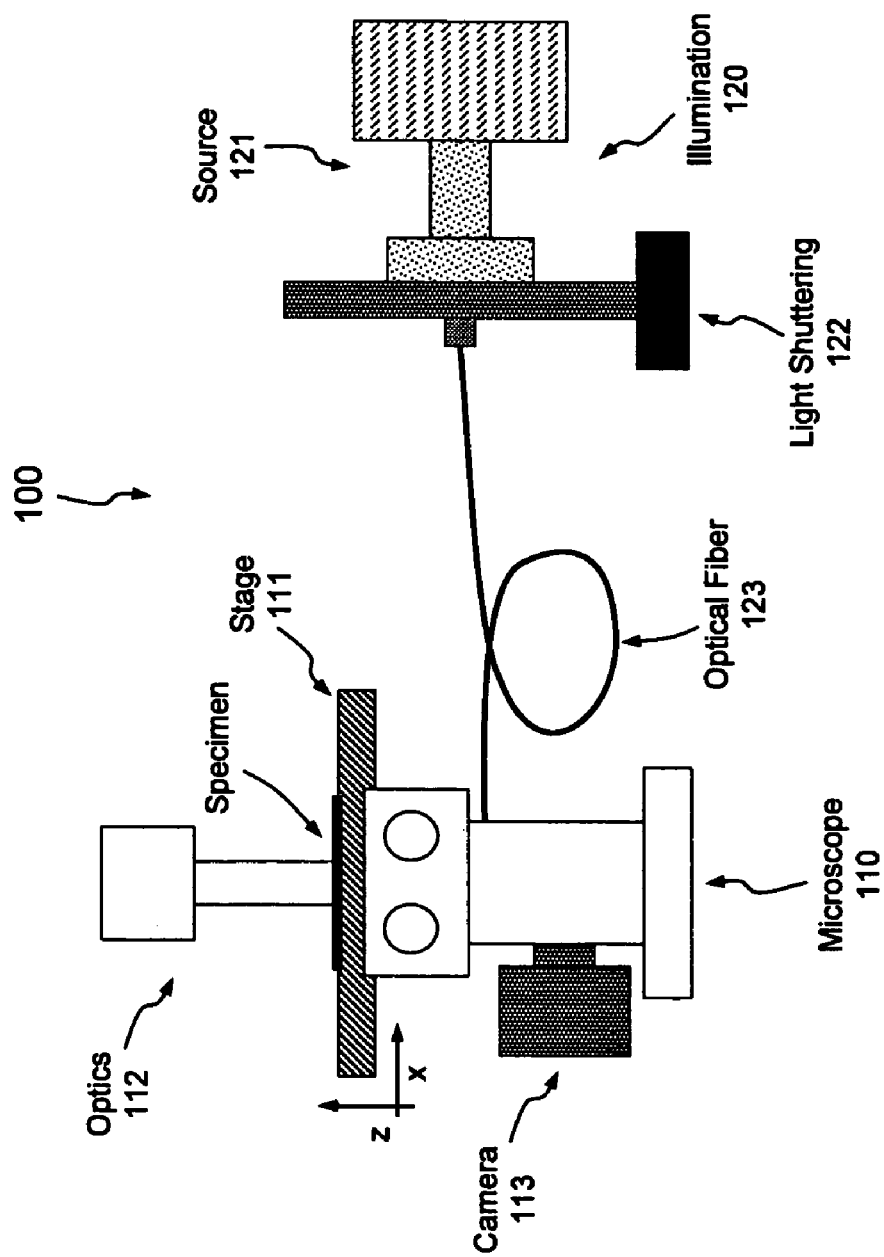
FIG. 1 is a simplified block diagram illustrating components of a microscope system with which embodiments of the present invention may be employed.
Figure 2:
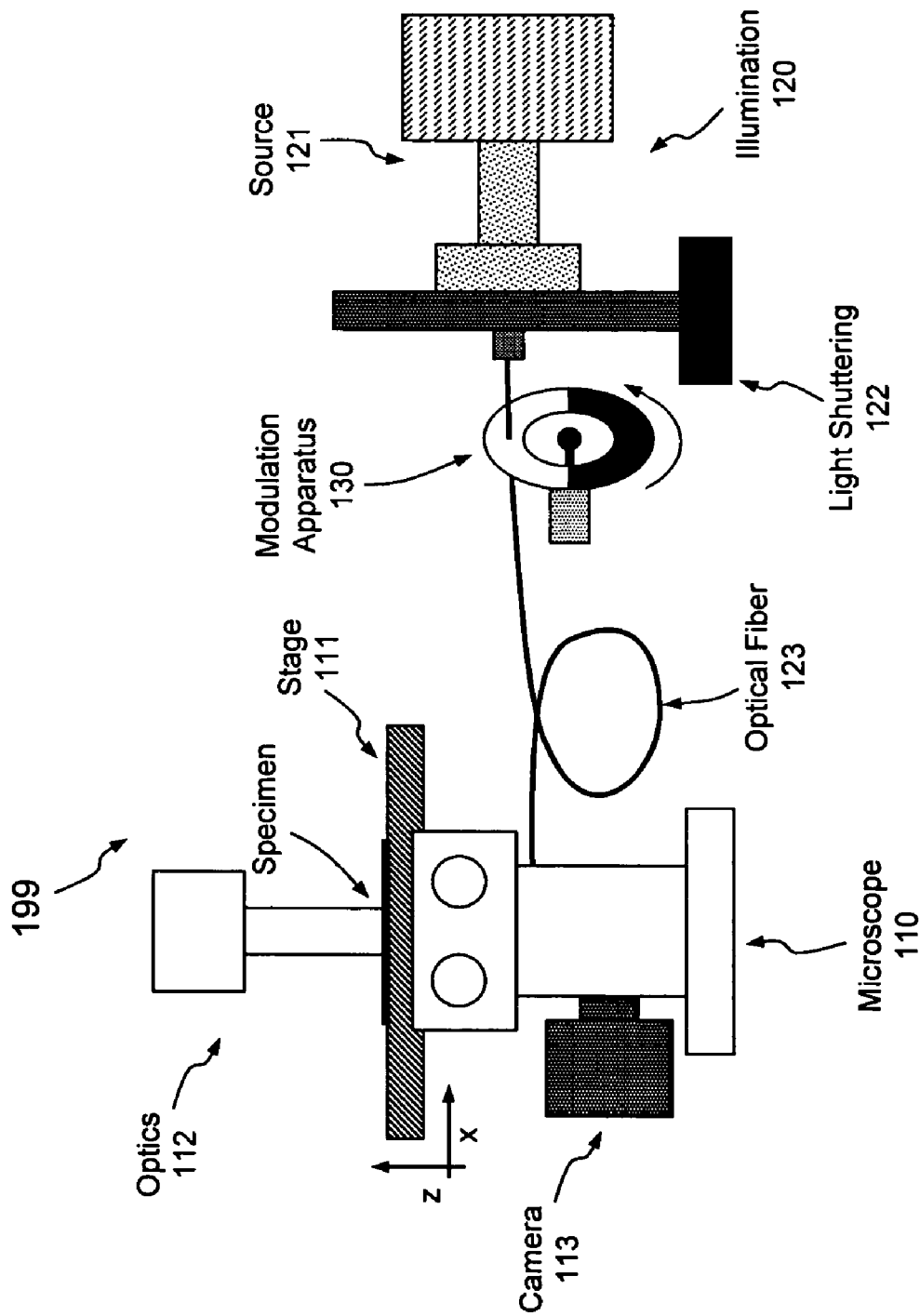
FIG. 2 is a simplified block diagram illustrating components of a microscope system employing one embodiment of a modified illumination system in accordance with the present disclosure.

Turning now to the drawing figures, FIG. 1 is a simplified block diagram illustrating components of a microscope system with which embodiments of the present invention may be employed, and FIG. 2 is a simplified block diagram illustrating components of a microscope system employing one embodiment of a modified illumination system in accordance with the present disclosure.

Specifically, FIG. 1 illustrates the structural components of a conventional system 100 configured and operative to illuminate a sample (or "specimen" in FIG. 1) for live-cell imaging on an inverted microscope system 110. Structural elements of system 100 are well known in the art, and only a brief description is provided herein. A typical conventional system 100 employs a microscope system 110 and an illumination delivery system 120.

Microscope system 110 generally comprises a stage 111, an optical system (optics) 112, and an imaging system, represented by camera 113 in FIG. 1. Stage 111, typically movable in three dimensions along axes generally designated as x, y, and z (where the y axis is orthogonal to the plane of FIG. 1), is operative to position the specimen along an optical path of optics 112. Optics 112 may be employed by a researcher or other user to view the specimen supported on stage 111, to assist in focusing thereof, to align camera 113 for imaging operations, or some combination thereof. In that regard, it is noted that camera 113 and optics 112 may be integrated or otherwise operably coupled, enabling camera 113 to benefit from focusing, magnification, resolution enhancement, or other optical effects provided by optics 112. Various electrical, mechanical, or electro-mechanical elements facilitating stage 111 positioning, characteristics and configuration of optics 112, and imaging parameters of camera 113 are generally known in the art and not depicted in FIG. 1.

Illumination delivery system 120 generally comprises a light source 121, a light shuttering system or apparatus 122, and an illumination or excitation light delivery path, represented by an optical fiber 123 in FIG. 1. In the exemplary FIG. 1 embodiment, and as is generally practiced in the art, illumination or excitation light is provided by source 121 through shuttering apparatus 122 along optical fiber 123 or another appropriate illumination path; excitation light is thus delivered to microscope system 110 for illumination of the specimen supported on stage 111. It will be appreciated that source 121 may be embodied in or comprise any of various types of light sources known to produce excitation light at a desired portion of the electromagnetic spectrum. In that regard, source 121 may be embodied in a broad-spectrum lamp, a light emitting diode (LED), a laser, or any other device configured and operative to produce light at a desired wavelength or range of wavelengths.

Figure 4A:
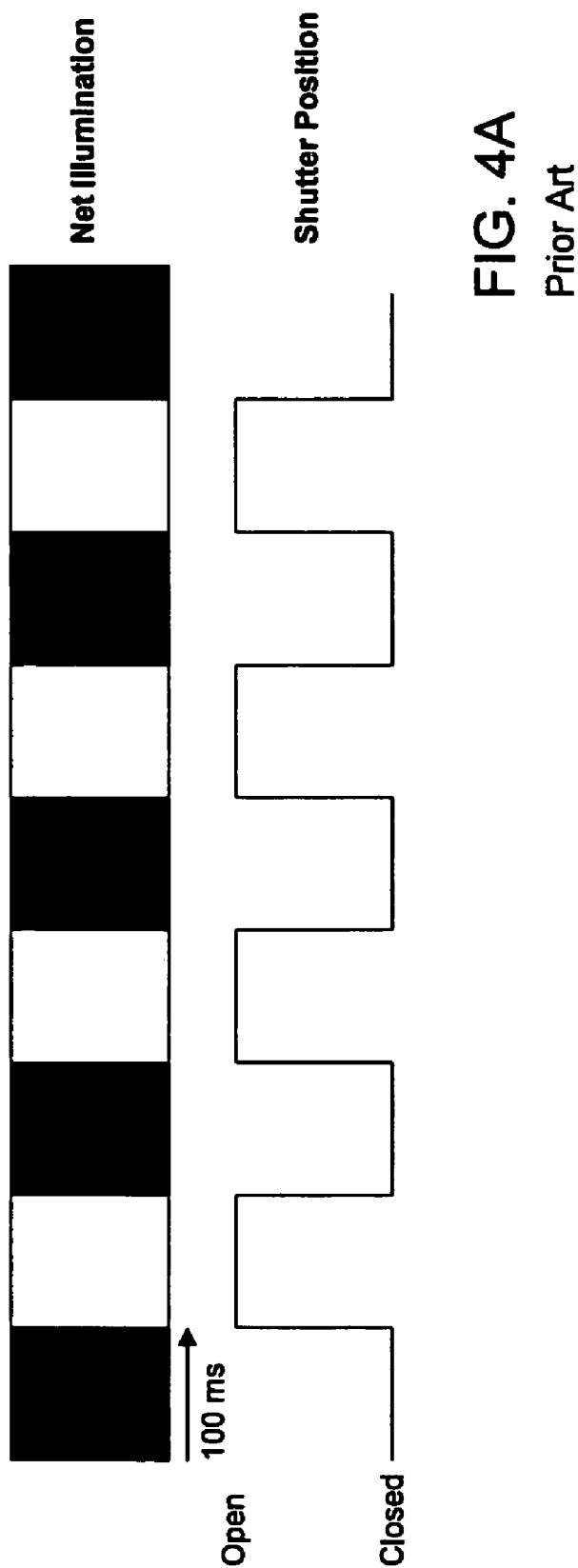
FIGS. 4A and 4B are simplified diagrams illustrating conventional and modified illumination system timings, respectively.

As noted above, the conventional system 100 illustrated in FIG. 1 may employ a shutter apparatus 122 interposed in the excitation path; shuttering apparatus 122 toggles illumination on and off. In that regard, FIG. 4A is a simplified diagram illustrating a conventional illumination system timing; specifically, the top portion of FIG. 4A depicts the net illumination provided to optical fiber 123 through shuttering apparatus 122. In conventional applications, net illumination is exclusively a function of shutter position (represented at the bottom portion of FIG. 4A), which varies over time.

During operation of shuttering apparatus 122, the full intensity of excitation light from source 121 is simply toggled, i.e., when the shutter is open, excitation light (in its full intensity as provided by source 121) is transmitted to optical fiber 123. In particular, the position of the shutter alternately enables and disables transmission of light to optical fiber 123, but neither adjusts, pulses, modulates, nor otherwise varies the intensity of the illumination delivered to optical fiber 123 and microscope system 110. In periods during which the shutter is open (i.e., the frame period), excitation illumination passing through shuttering apparatus 122 is at a constant intensity, represented by the white portions of the net illumination plot.

As noted above, FIG. 2 illustrates components of a system 199 which employs an embodiment of a illumination system 120 modified in accordance with the present disclosure. Additionally, FIGS. 3A and 3B are simplified block diagrams illustrating structural components of one embodiment of a modulation apparatus operative in cooperation with such a modified illumination system 120. In the exemplary FIG. 2 embodiment, the conventional system 100 of FIG. 1 has been modified to include an advanced illumination system 120 configured and operative to deliver pulsed light through a modulation apparatus 130 to microscope system 110. Specifically, illumination intensity may be pulsed at a super-excitation reducing rate, i.e., intensity may be modulated at a predetermined frequency operative to reduce re-excitation of molecules already in the excited state, minimizing the number of electrons in the super-excited state. In the FIG. 2 embodiment, illumination pulsing through modulation apparatus 130 may be in series with operation of the shutter in shuttering apparatus 122; accordingly, modification or alteration of additional components of system 199 may be unnecessary, and the operational or functional characteristics thereof may remain substantially as set forth above with reference to FIG. 1.

As indicated in FIG. 2, the foregoing pulsing effect may be achieved by integration of modulation apparatus 130 into illumination delivery system 120. In some embodiments, for example, modulation apparatus 130 may employ a mechanical "light chopper" 139 situated in the light path represented by optical fiber 123; one embodiment of such a chopper 139 is illustrated in more detail in FIGS. 3A and 3B. In the exemplary implementation, chopper 139 generally comprises a wheel or disk 136 having a substantially opaque portion 137 and a substantially transparent portion 138. During operation, disk 136 may be rotated about a hub or axis 135 by a motor 134 at a selected or predetermined rotational velocity; such rotation alternately interposes transparent portion 138 (FIG. 3A) and opaque portion 137 (FIG. 3B) into the excitation light delivery path represented by optical fiber 123.

As represented by the solid optical fiber 123 in FIG. 3A, transparent portion 138 of disk 136 allows transmission of excitation light and delivery thereof to microscope system 110. It will be appreciated that appropriate selection of material for transparent portion 138 may depend upon the wavelength or intensity of the excitation light provided by source 121, for example, or other factors such as: operational requirements, capabilities, and limitations of microscope system 110; functional characteristics of optics 112 and camera 113; length and attenuation factors associated with the excitation light delivery path (e.g., optical fiber 123); prescribed or optimal protocols for specific imaging applications; and other system considerations.

Conversely, as represented by the dashed optical fiber 123 in FIG. 3B, opaque portion 137 of disk 136 does not allow transmission of excitation light along the optical path to microscope system 110. As with transparent portion 138, appropriate selection of material for opaque portion 137 may depend upon various factors and system parameters, one of which is the requirement that opaque portion 137 be operative selectively to attenuate electromagnetic energy (at a particular wavelength or range of wavelengths) provided by source 121.

Rotation of disk 136 allows intermittent transmission and interruption of illumination from source 121 through optical fiber 123; illumination intensity may be pulsed through such interruption at a selected and adjustable frequency independent of shutter operation at shuttering apparatus 122. The diameter and rotational velocity of disk 136, as well as the relative sizes of opaque portion 137 and transparent portion 138, may affect the frequency at which illumination intensity is pulsed through disk 136. It will be appreciated that various configurations of disk 136 are contemplated, including embodiments employing multiple opaque and transparent portions, arranged annularly in a desired relationship to pulse unattenuated excitation light at a super-excitation reducing rate.

Figure 4B:
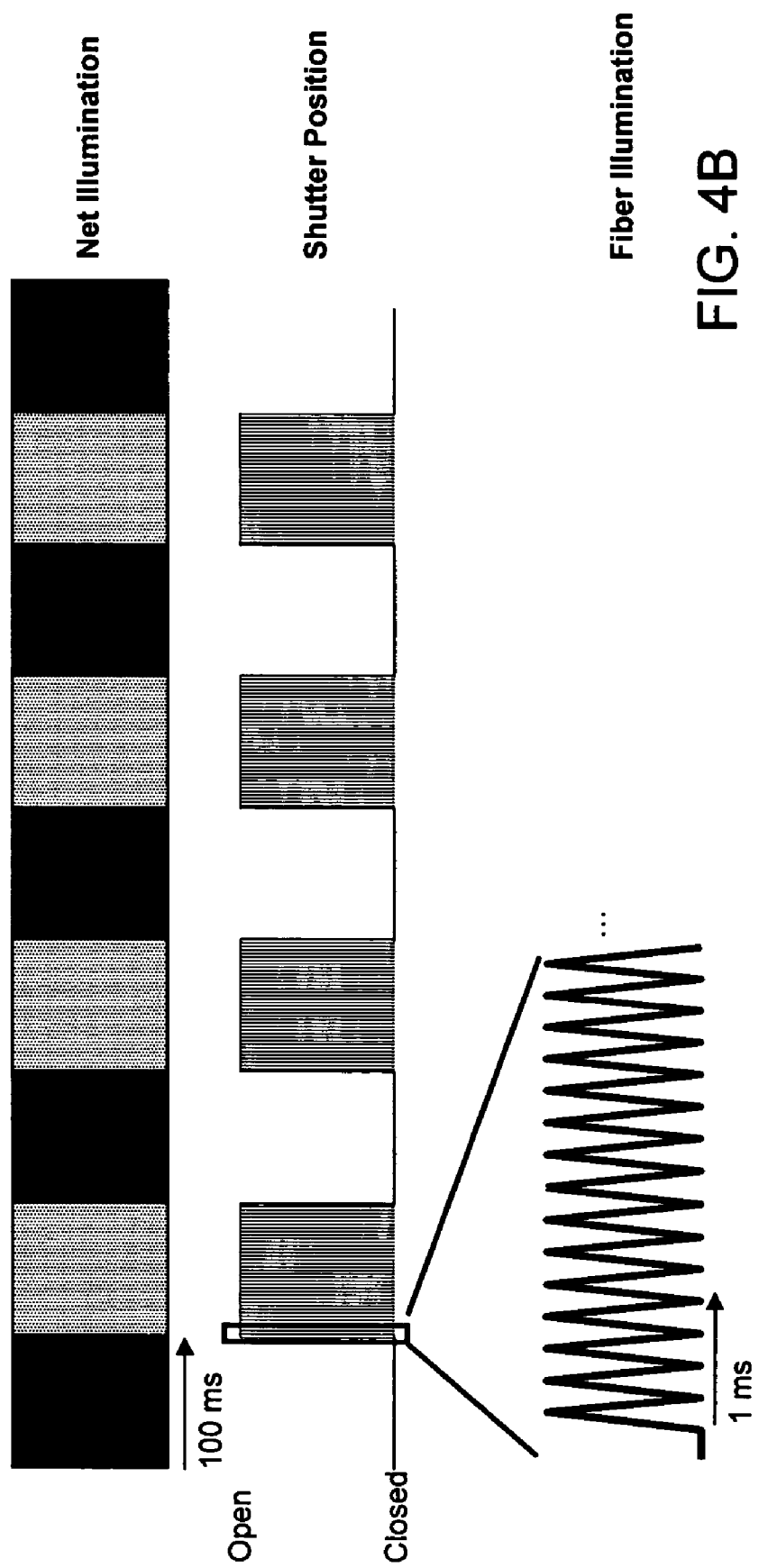

In operation of modified system 199, during the shutter open time of shuttering apparatus 122, excitation light is pulsed through modulation apparatus 130, such as chopper 139, at a super-excitation reducing frequency. In that regard, FIG. 4B is a simplified diagram illustrating modified illumination system timing; specifically, the top portion of FIG. 4B depicts the net illumination provided to microscope system 110 through the combination of shuttering apparatus 122 and modulation apparatus 130. Shutter position is represented at the center of FIG. 4B, while light delivered along optical fiber 123 is represented at the bottom portion of FIG. 4B.

During operation of modulation apparatus 130 in cooperation with shuttering apparatus 122, the full intensity of excitation light from source 121 is not simply. toggled; rather, light passing through modulation apparatus 130 is pulsed, selectively varying the intensity of the illumination delivered to optical fiber 123 and microscope system 110. In periods during which the shutter is open, excitation illumination passing through the combination of shuttering apparatus 122 and modulation apparatus 130 is at a varying intensity, represented by the gray portions of the net illumination plot.

The pulse rate or frequency of the illumination modulation may be selectively adjusted such that all (or a desired percentage of) excited electrons have a chance to relax before the next pulse of light is introduced. For most fluorochromes, pulses at a rate of approximately one per $10^{-8}$ seconds, or on the order of approximately 100 MHz, may provide a suitable interval allowing appropriate relaxation. While pulses at a frequency of 100 MHz may virtually eliminate the likelihood of super-excitation in most applications, it is not necessarily true that the rate of illumination modulation must be high. In particular, any illumination method or strategy that reduces the likelihood of re-excitation of already excited electrons will facilitate reduction of photobleaching and photodamage. Since fluorochrome excitation is a statistical event, any high modulation rate (e.g., in the range of about 100 KHz to about 1 GHz) will reduce the likelihood of super-excitation. Within this range, the modulated illumination may be selected to be less than saturating (i.e., not causing fluorochrome saturation) to prevent photodamage and photobleaching. Those of skill in the art will appreciate that certain frequencies may be more suitable than others for specific applications, and may depend upon, among other factors, specific fluorochromes or chemistry of the target molecules illuminated at microscope system 110. The present disclosure is not intended to be limited by any particular re-excitation reducing frequency or frequency range.

Various methods may be employed to provide modulation of illumination intensity at one or more selected frequencies. For example, a mechanical or electromechanical component, such as light chopper 139 described above with reference to FIGS. 2–3B (or a combination of other mechanical components), may be interposed between source 121 and microscope system 110 in the excitation light delivery path. Such a mechanical or electromechanical element may be suitably configured (e.g., dimensioned and provided with sufficient rotational velocity) and operative to accommodate frequencies as high as 100 MHz or greater. In addition to rotating disks such as in the exemplary embodiment, "blades," mirrors, optical gratings, or other simple rotating devices and structures may also be used in mechanical modulation embodiments. Additionally or alternatively, electromechanical elements, such as digital micro-mirror devices, for example, may also be employed.

Where mechanical or electromechanical elements are employed to provide illumination modulation, a system 199 such as illustrated in FIG. 2 may be implemented primarily with conventional components; modifications may readily be effectuated by inserting an appropriate modulation apparatus 130 (such as chopper 139) in the light delivery path.

Given the functional considerations set forth above, it will be appreciated that additional embodiments may be implemented with specialized or proprietary light sources. Accordingly, modulation apparatus 130 (e.g., mechanical or electromechanical components) may be eliminated from the light delivery path if an appropriately functional light source 121 is employed. For example, a light emitting diode (LED), flash lamp, or pulsed laser (such as a non-continuous wave laser) may be configured and operative to provide modulated illumination intensities directly from source 121. Specifically, any method of generating excitation light at source 121 that divides the illumination field (defined by the shutter open period of shuttering apparatus 121) into sub-regions that are significantly smaller than the full illumination field (as set forth above with reference to FIG. 4B) may produce intensity modulation rates appropriate for reducing super-excitation. As noted above, such frequencies may include, for example, frequencies between 100 KHz and 1 GHz.

Accordingly, a system 100 such as illustrated in FIG. 1 may also be implemented with a modified light source 121 to provide modulated illumination intensities in accordance with the present disclosure. It will be appreciated that light source 121 in such embodiments may be selected in accordance with a desired wavelength of output excitation light, maximum or optimal modulation rate capabilities, power consumption, the length and attenuation properties of the excitation light delivery path (such as optical fiber 123), and other considerations.

Figure 5:
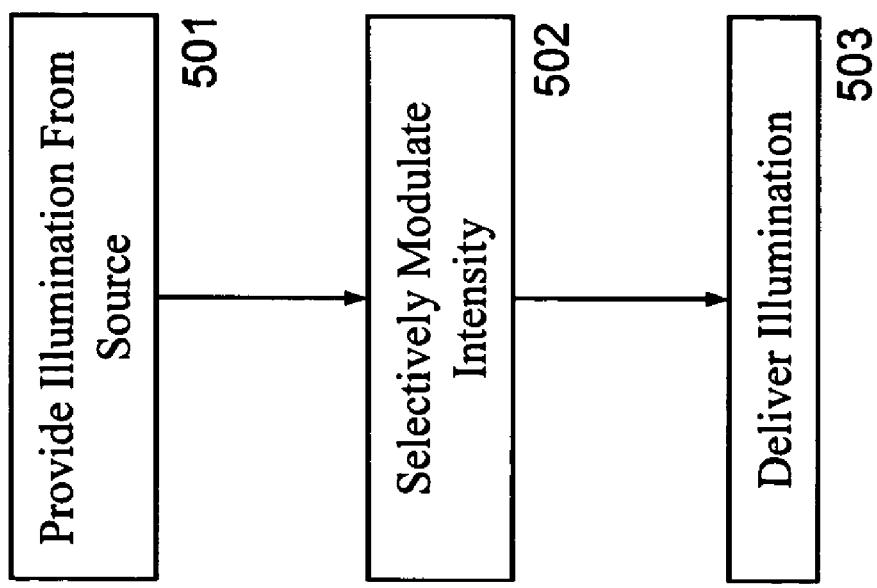
FIG. 5 is a simplified flow diagram illustrating functional characteristics of one method of reducing super-excitation.
Figure 6:
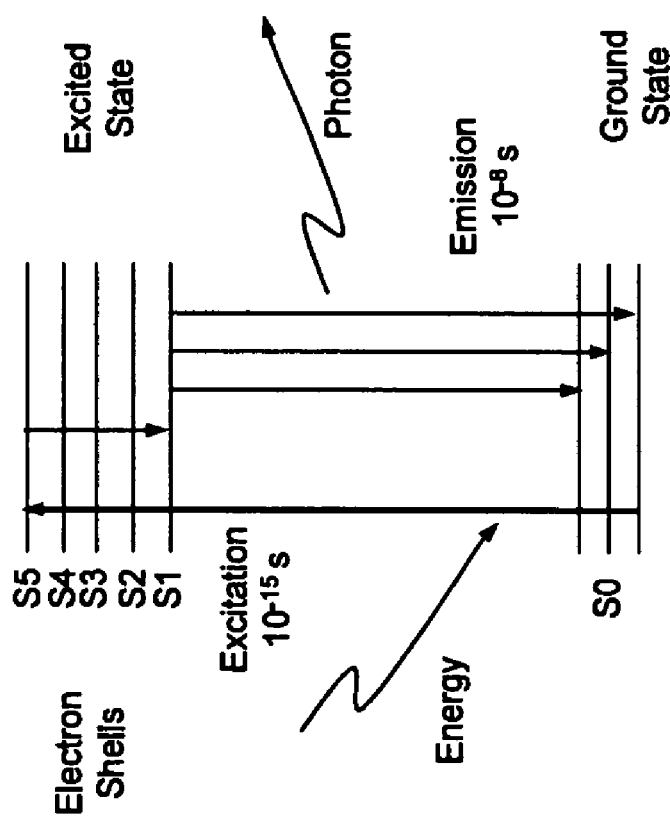
FIG. 6 is a Jablonski diagram illustrating fluorescence emissions.

FIG. 5 is a simplified flow diagram illustrating functional characteristics of one method of reducing super-excitation of target molecules. As indicated at block 501, illumination may be provided, such as by a light source described herein. At block 502, an intensity of the provided illumination may be selectively modulated in accordance with the considerations set forth in detail above at a frequency operative to reduce, minimize, or eliminate re-excitation of molecules or electrons already in an excited state. Such modulated illumination may then be provided to an imaging system as indicated in block 503.

As depicted in FIG. 5, the modulating operation at block 502 may be facilitated by a modulation apparatus, embodied in or comprising mechanical or electromechanical components, interposed between the source and the imaging system. By way of example, such an arrangement may result in selective or intermittent interruption of the providing depicted at block 501; this interruption may be at a super-excitation reducing frequency. Additionally or alternatively, the modulating at block 502 may be effectuated through selective pulsing of the intensity of illumination provided from the source itself. Such pulsing may generally comprise varying the output of illumination from the source during the providing at block 501. Specifically, in some exemplary embodiments (not shown in FIG. 5) employing a suitable light source (such as an LED or pulse laser, for example), the operations depicted at blocks 501 and 502 may be combined, such that appropriately modulated illumination may be provided directly from the source.

In accordance with the foregoing method, a 100 MHz modulation frequency may provide illumination intensities of up to full fluorochrome saturation (i.e., all molecules are in the excited state) without creating significant photobleaching or photodamage. In one exemplary embodiment, the modulation frequency may be selected to be greater than the excitation half-time of fluorophores in the sample (i.e., target molecule) up to one tenth of the shutter exposure rate (i.e., the period during which the shutter at shuttering apparatus 121 is open).

Several features and aspects of the present invention have been illustrated and described in detail with reference to particular embodiments by way of example only, and not by way of limitation. Those of skill in the art will appreciate that alternative implementations and various modifications to the disclosed embodiments are within the scope and contemplation of the present disclosure. Therefore, it is intended that the invention be considered as limited only by the scope of the appended claims.

The invention claimed is:

1. A method comprising:
   providing illumination from a source;
   selectively modulating an intensity of said illumination at a frequency operative to reduce re-excitation of excited sample molecules; and
   delivering said illumination to an imaging system in accordance with said selectively modulating.

2. The method of claim 1 wherein said selectively modulating comprises pulsing said intensity of said illumination at said frequency.

3. The method of claim 2 wherein said pulsing comprises varying an output of illumination from said source during said providing.

4. The method of claim 3 wherein said pulsing comprises utilizing a non-continuous wave laser.

5. The method of claim 3 wherein said pulsing comprises utilizing a light emitting diode.

6. The method of claim 1 wherein said selectively modulating comprises interrupting said providing at said frequency.

7. The method of claim 6 wherein said interrupting comprises utilizing a mechanical device.

8. The method of claim 6 wherein said interrupting comprises utilizing an electro-mechanical device.

9. The method of claim 6 wherein said interrupting comprises electrical interruption of said providing from said source.

10. The method of claim 1 wherein said frequency is greater than the excitation half-time of fluorophores in said sample molecules up to one tenth of a shutter exposure rate.

11. The system of claim 1 wherein said imaging system includes a camera.

12. A system comprising:
an imaging system;
an excitation light delivery system comprising an illumination source; said delivery system operative to deliver illumination from said source to illuminate sample molecules at said imaging system; and
modulation means for selectively modulating an intensity of said illumination at a frequency operative to reduce re-excitation of excited ones of said sample molecules.

13. The system of claim 12 wherein said modulation means comprises a mechanical apparatus interposed between said source and said imaging system.

14. The system of claim 13 wherein said mechanical apparatus is a rotating light chopper.

15. The system of claim 12 wherein said modulation means is coupled to said source and comprises an electrical mechanism operative to vary an output of illumination from said source.

16. The system of claim 15 wherein said source is a non-continuous wave laser.

17. The system of claim 15 wherein said source is a light emitting diode.

18. The system of claim 12 wherein said imaging system is for acquiring images of said sample molecules.

19. A system for illuminating live cells; said system comprising:
an illumination source;
an imaging system operative to acquire images of sample molecules;
an excitation light delivery path delivering illumination from said source to illuminate said sample molecules at said imaging system; and
a modulation apparatus interposed between said source and said imaging system in said delivery path; said modulation apparatus modulating an intensity of said illumination at a frequency operative to reduce re-excitation of excited ones of said sample molecules.

20. The system of claim 19 wherein said modulation apparatus is a light chopper.

21. The system of claim 19 wherein said modulation apparatus is a digital micro-mirror.

22. A system comprising:
an illumination source; and
an imaging system receiving illumination from said source and operative to acquire images of sample molecules;
wherein said source modulates an intensity of said illumination at a frequency operative to reduce re-excitation of excited ones of said sample molecules.

23. The system of claim 22 wherein said source is a pulsed laser.

24. The system of claim 22 wherein said source is a light emitting diode.

25. The system of claim 22 wherein said frequency is greater than about 100 KHz.

* * * * *